United States Patent [19]

Oishi

[11] 3,953,365
[45] Apr. 27, 1976

[54] CATALYST FOR DEHYDROCYCLIZATION OF PARAFFINS

[75] Inventor: Masayoshi Oishi, Wilmington, Del.

[73] Assignee: Sun Ventures, Inc., St. Davids, Pa.

[22] Filed: Aug. 22, 1974

[21] Appl. No.: 499,695

Related U.S. Application Data

[60] Continuation-in-part of Ser. No. 356,002, April 30, 1973, abandoned, which is a division of Ser. No. 250,991, May 8, 1972, Pat. No. 3,775,502.

[52] U.S. Cl............................................. 252/455 Z
[51] Int. Cl.²......................................... B01J 29/06
[58] Field of Search ................................ 252/455 Z

[56] References Cited
UNITED STATES PATENTS

| | | | |
|---|---|---|---|
| 3,376,215 | 4/1968 | Bertolacini et al............. | 252/455 Z |
| 3,437,586 | 4/1969 | Weisz............................ | 252/455 Z |
| 3,527,836 | 9/1970 | Turner et al.................. | 252/455 Z |

Primary Examiner—Carl F. Dees
Attorney, Agent, or Firm—J. Edward Hess; Donald R. Johnson; Anthony Potts, Jr.

[57] ABSTRACT

Process of dehydrocyclizing $C_6$–$C_{10}$ paraffins using a sodium zeolite X or sodium zeolite Y, which zeolite has been ion exchanged with from 0.10 to 1.2 weight percent platinum, the catalyst calcined and the platinum then reduced with hydrogen to the free metal. Said catalyst is characterized by its rather high platinum dispersion. In an especially preferred aspect of the invention, the catalyst is given a final ion exchange with a sodium salt such as sodium bicarbonate. The dehydrocyclization reaction is carried out at from 500° to 560°C and preferably from 510° to 555°C using a partial pressure of hydrogen of from 10 to 300 p.s.i.g. and preferably 50 to 200 p.s.i.g. to form benzene and alkylbenzenes.

3 Claims, No Drawings

CATALYST FOR DEHYDROCYCLIZATION OF PARAFFINS

CROSS REFERENCE TO RELATED APPLICATIONS

This application is a continuation-in-part of application Ser. No. 356,002, filed Apr. 30, 1973, now abandoned which is a divisional of application Ser. No. 250,991, filed May 8, 1972, now U.S. Pat. No. 3,775,502, issued Nov. 27, 1973.

BACKGROUND OF THE INVENTION

In the processing of petroleum into gasoline, it is known that normal paraffins are undesirable gasoline components because of their very low octane ratings. Generally modern refining technology calls for reforming the straight run gasoline fraction using a supported noble metal catalyst. Generally this reforming is carried out at 450 to 500 p.s.i. and converts naphthenes into aromatics and normal paraffins into isoparaffins. It is also known that the normal paraffins can be removed from the straight run gasoline by means of mole sieves. This is not generally carried out commercially because of the expense involved and the extremely low value of one of the products, namely, the normal paraffins. The present invention is directed to upgrading these normal paraffins into high octane gasoline components particularly aromatics. These aromatics have a wide variety of other well known uses such as solvents, etc.

U.S. Pat. No. 3,527,836, dated Sept. 8, 1970, discloses a catalyst prepared by adding platinum to a zeolite by ion exchange. The pore size of the zeolite is equal to or less than that of a 5A type sieve. The catalyst is useful for dehydrogenating alkanes to alkenes.

U.S. Pat. No. 3,376,215, dated Apr. 2, 1968, discloses a catalyst prepared by impregnating a particular form of zeolite known as mordenite with platinum.

SUMMARY OF THE INVENTION

The present invention relates to the dehydrocyclization of paraffins and particularly normal paraffins containing from 6 to 10 carbon atoms to form aromatic compounds.

The catalyst used in the present invention is a zeolite which has been ion exchanged with platinum and then had the platinum reduced to the free metal state. This catalyst has been found to be superior for catalyzing dehydrocyclization of paraffins to similar catalyst which have been prepared by simply impregnating the zeolite with platinum. The zeolites used in the present invention are sodium zeolite X and sodium zeolite Y; said zeolites having an aperture size of 8 angstroms (A). Zeolite X has the typical formula:

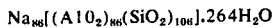

Zeolite Y has the typical formula:

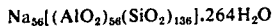

A further description of these zeolites may be found in "Crystalline Molecular Sieves" by D. W. Breck, JOURNAL OF CHEM., 41, 678–689 (1964).

Zeolite X is preferred because zeolite Y has a greater tendency to coke up during the dehydrocyclization reaction.

DESCRIPTION

After the desired zeolite is obtained, it is ion exchanged with from 0.10 to 1.2 weight percent platinum. Below about 0.10 percent platinum, the catalyst is not sufficiently active. Above about 1.2 percent platinum, insufficient improvement in catalyst activity is obtained to warrant more use of expensive platinum. The zeolite is ion exchanged with platinum by treatment with an aqueous solution of both a sodium salt of a strong acid and a soluble platinum salt at a moderate temperature for several hours. Generally this treatment is carried out at from 25° to 80°C for a period of from 1 to 24 hours. The ion exchange solution generally will contain from $1 \times 10^{-4}$ to 0.1 molar platinum and from 1 to 10 molar sodium. The pH of the ion exchange solution ordinarily will be from 7 to 9. The catalyst is then washed thoroughly with a solvent such as water to remove the salt residue and is then dried and ground. The catalyst is then calcined by heating at from 400° to 650°C in an oxygen-containing atmosphere such as air or pure oxygen for from 1 to 6 hours. Then the platinum is reduced to the free metal by treatment with flowing hydrogen for 1 to 4 hours at 350° to 550°C. The resulting catalyst has improved activity as compared with a similar catalyst which has been simply impregnated with platinum.

An alternative way of generally preparing the zeolite catalyst of present invention is to ion exchange the zeolite by treatment with a soluble platinum salt at a moderate temperature for several hours. Again this treatment is carried out at from 25° to 80°C for a period of from 1 to 24 hours. Then the catalyst is finished in a similar fashion as described in the foregoing paragraph.

In a typical preparation, a large quantity of zeolite X such as 100 g. is air dried in an oven overnight at 110°C. A ten gram sample of the dried zeolite X is added to a flask containing 200 ml. of distilled water and 61.4 g. of NaCl. This mixture is stirred for 15 minutes while the temperature is maintained at 60°C. A solution of 0.2 g. of $Pt(NH_3)_4Cl_2 \cdot H_2O$ in 100 ml. of distilled water is added dropwise to the contents of the flask. The resulting slurry is stirred overnight while being maintained at 60°C. The resulting mixture is filtered and the resulting cake-like catalyst is washed thoroughly with distilled water until it is substantially free of chlorine. The catalyst is dried for 2 hours at 100°C in an oven after which it is hand ground until it passes through a No. 40 mesh screen (U.S. Sieve Series). The catalyst is then calcined at 500°C with 10 cc/min of air flowing. The final temperature is reached in about 2 hours. The catalyst is reduced with hydrogen in the reactor before the runs.

In an especially preferred embodiment of the present invention, the catalyst is given a final treatment with an aqueous sodium bicarbonate salt. This serves to convert the $H^+$ zeolite sites, which were created when the platinum was reduced to the free state, back to Na zeolite sites, providing a catalyst substantially free of acid zeolite sites. Generally, this treatment should be done with a sodium salt solution having pH of greater than 8. The solution should be diluted and generally will be from 0.01 to 1 normal. The catalyst generally is treated for from 1 to 24 hours at from 25° to 80°C. The anionic position of the sodium salt should be one which is readily removable from the zeolite. Thus sodium carbonate and sodium bicarbonate are preferred for this use. A preparation of such a catalyst involves treating 10 grams of the platinum ion exchanged and reduced X-type zeolite described above with 100 ml of a 0.1N NaHCO₃ aqueous solution for 12 hours at 60°C.

The catalysts of the present invention contain the platinum in substantially the mono molecular free metal state due to each platinum ion having been associated with an individual Pt$^{(+)}$ zeolite$^{(-)}$ site and then reduced to the Pt° H⁺Z$^{(-)}$ state wherein individual molecules of free platinum metal are physically located adjacent individual H⁺Z$^{(-)}$ sites. The platinum dispersion of the catalyst used in the Examples has been found to be 94.3%. The catalysts of the present invention have platinum dispersions of at least 50%; preferably a dispersion in excess of 60% and more preferably a dispersion between 65–99.9%.

Due to the high dispersion of platinum in the present catalysts, the presence of chlorine which is often used to aid in the dispersion of the platinum is unnecessary and in fact undesirable due to the otherwise deleterious effect of chlorine on the dehydrocyclization activity of the catalyst. Thus the catalyst should contain less than 0.20 weight percent chlorine.

The dehydrocyclization is generally carried out using a liquid hourly space velocity as based on feed of from 0.1 to 40 and preferably from 2 to 15. The dehydrocyclization is carried out at from 500° to 560°C and preferably from 510° to 550°C. Above 555°C and especially above 560°C the amount of cracking taking place starts to increase rapidly. Below 500°C the amount of conversion of the paraffin is too low. The amount of cyclization as opposed to the amount of isomerization increases considerably at about 510°C.

The dehydrocyclization is carried out under moderate pressure expressed herein in terms of partial pressure of hydrogen in the reactor. The partial pressure of hydrogen generally is from 10 to 300 p.s.i.g. with from 50 to 200 p.s.i.g. being the preferred range. Below 50 p.s.i.g. and especially below 10 p.s.i.g. coking of the catalyst becomes too rapid to be economical. As the pressure increases above 200 p.s.i.g. and especially above 300 p.s.i.g., the cracking and isomerization reactions become favored instead of the dehydrocyclization reaction.

Suitable paraffinic starting materials contain 6 to 10 carbon atoms. Any paraffin containing from 6 to 10 carbon atoms is suitable. Generally, the normal paraffins are preferred because due to their low octane numbers, they can be improved more than the branched paraffins which have higher octane numbers. Ordinarily the feed stream will be the normal hydrocarbons removed by denormalization of a $C_6$–$C_{10}$ petroleum stream which would consist essentially of $C_6$–$C_{10}$ normal hydrocarbons.

In Examples 1 to 18 a pulse microreactor is used. This reactor is a stainless steel tube about 200 mm. long and having an inside diameter of 4 mm. The inside of the tube contains pyrex wool retainers which keep the catalyst in place. In each of the Examples, the tube is packed with 0.125 g of catalyst. The tube is fitted in a brass mounting sleeve which contains a thermocouple in a well. The brass sleeve in turn mounted in a 4-inch electric furnace operated on 115 volts and controlled by a 7.5 amp powerstat. The top of the tube is fitted with a silicone rubber septum mounted in a septum holder and a carrier gas inlet. The carrier gas is deoxygenated by hydrogen passed through the system at a rate of about 50 cc per minute under the pressure indicated in the particular example being reported. The catalyst is preconditioned by injecting a 30 microliter pulse of the n-heptane which is being dehydrocyclized. The reactor effluent from this injection is not analyzed. A 2 microliter charge of the material being dehydrocyclized is then injected through the septum and the resultant effluent is programmed through a previously calibrated gas chromatograph. The definitions of selectivity reported in the Table are:

$$\% \text{ cyclization} = \frac{\text{aromatics (wt. \%)} + \text{naphthenes}}{\text{conversion (wt. \%)}} \times 100$$

$$\% \text{ isomerization} = \frac{\text{total isomers of same number of carbon atoms (wt. \%)}}{\text{conversion (wt. \%)}} \times 100$$

$$\% \text{ cracking} = \frac{\text{total of lesser numbered carbon atoms (wt. \%)}}{\text{conversion (wt. \%)}} \times 100$$

The cyclization to cracking ratio shown in the Table to the right of the cracking selectivity results from the division the % cyclization by the % cracking selectivities. The larger this value the better the catalyst for dehydrocyclization.

The six catalysts used in the Examples are prepared in accordance with the typical catalyst preparations described above. The hydrogen reduction of the catalyst was carried out for 2 hours. In all the Examples, the ion exchange solution contained 0.2 g. Pt(NH₃)₄Cl₂·H₂O in 100 ml. of the solution indicated and the treatment was carried out at 60°C for 16 hours.

TABLE

DEHYDROCYCLIZATION OF n-HEPTANE

| | CATALYST PREPARATION | | | | DEHYDROCYCLIZATION | | | | |
|---|---|---|---|---|---|---|---|---|---|
| | | | | | | SELECTIVITY | | | |
| EXAMPLE | ION EXCHANGE | POST TREATMENT | TEMP. °C | PRES-SURE psig | CONVER-SION % | CYCLI-ZATION % | ISOMER-IZATION % | CRACK-ING % | CYCL/CRACK-ING |
| 1 | 0.25% Pt/NaX, 0.07% Cl (Pt ion exchanged in 5.25M NaCl aqueous solution) | Cat. reduced at 500°C with 50 cc H₂/min | 510 | 150 | 23.9 | 21.4 | 26.5 | 52.2 | 0.41 |
| 2 | " | " | 510 | 100 | 27.0 | 38.7 | 23.0 | 38.3 | 1.01 |
| 3 | " | " | 510 | 50 | 41.9 | 53.8 | 22.0 | 24.2 | 2.26 |
| 4 | 0.25% Pt/NaX, 0.07% Cl | Cat. reduced at 500°C with 250 cc H₂/min | 510 | 150 | 33.9 | 29.2 | 27.4 | 43.4 | 0.67 |
| 5 | " | " | 510 | 100 | 44.1 | 39.3 | 30.1 | 30.6 | 1.31 |
| 6 | " | " | 510 | 50 | 58.7 | 60.2 | 21.2 | 18.6 | 3.24 |
| 7 | 0.30% Pt/NaX, | Cat. reduced | 510 | 150 | 29.2 | 19.8 | 33.1 | 47.1 | 0.42 |

TABLE-continued

| | CATALYST PREPARATION | | | | DEHYDROCYCLIZATION OF n-HEPTANE | | | | |
| | | | | | | DEHYDROCYCLIZATION | | | |
| | | | | | | | SELECTIVITY | | |
| EXAMPLE | ION EXCHANGE | POST TREATMENT | TEMP. °C | PRES- SURE psig | CONVER- SION % | CYCLI- ZATION % | ISOMER- IZATION % | CRACK- ING % | CYCL/ CRACK- ING |
|---|---|---|---|---|---|---|---|---|---|
| 8 | 0.04% Cl (Pt ion exchanged in 2.63M NaCl) | at 500°C with 50 cc H₂/min | | | | | | | |
| 9 | '' | '' | 510 | 100 | 33.6 | 30.9 | 31.8 | 37.4 | 0.83 |
| 10 | '' | '' | 510 | 50 | `52.2 | 52.0 | 24.8 | 23.2 | 2.24 |
| | 0.30% Pt/NaX, 0.04% Cl | Cat. reduced at 500°C with 250 cc H₂/min | 510 | 150 | 67.5 | 23.0 | 24.4 | 52.6 | 0.44 |
| 11 | '' | '' | 510 | 100 | 67.0 | 40.0 | 26.3 | 33.7 | 1.19 |
| 12 | '' | '' | 510 | 50 | 77.6 | 53.6 | 18.8 | 27.6 | 1.94 |
| 13 | 0.27% Pt/NaX, 0.02% Cl | Cat. reduced at 500°C with 50 cc H₂/min post treat with 0.1 N NaHCO₃ | 500 | 100 | 26.5 | 44.2 | 34.2 | 21.7 | 2.04 |
| 14 | '' | '' | 520 | 100 | 52.7 | 51.1 | 31.8 | 17.2 | 2.97 |
| 15 | '' | '' | 550 | 100 | 92.0 | 63.0 | 8.2 | 28.8 | 2.19 |
| 16 | 0.27% Pt/NaX, 0.02% Cl | Cat. reduced at 500°C with 50 cc H₂/min | 500 | 100 | 58.8 | 22.5 | 42.0 | 35.5 | 0.64 |
| 17 | '' | '' | 520 | 100 | 77.1 | 37.8 | 25.4 | 36.8 | 1.03 |
| 18 | '' | ''550 | 100 | 99.3 | 60.7 | 1.3 | 38.0 | 1.6 | |

The invention claimed is:

1. A catalyst consisting essentially of sodium zeolite X or sodium zeolite Y which zeolite contains from 0.10 to 1.2 weight percent platinum having a dispersion of at least 50% and less than 0.10 weight percent chlorine and is substantially free of acid zeolite sites.

2. Catalyst according to claim 1 wherein the platinum has a dispersion in excess of 60%.

3. Catalyst according to claim 1 wherein the platinum has a dispersion of between 65–99.9%.

* * * * *